United States Patent [19]

Gross et al.

[11] Patent Number: 5,157,252
[45] Date of Patent: Oct. 20, 1992

[54] PHOTOMETER ARRANGEMENT WITH SCATTERED LIGHT TRAP

[75] Inventors: Jürgen Gross, Hofheim am Taunus; Rudolf Kressirer, Frankfurt am Main, both of Fed. Rep. of Germany

[73] Assignee: Behringwerke Aktiengesellschaft, Marburg, Fed. Rep. of Germany

[21] Appl. No.: 740,142

[22] Filed: Aug. 5, 1991

[30] Foreign Application Priority Data

Aug. 7, 1990 [DE] Fed. Rep. of Germany ....... 4024954

[51] Int. Cl.$^5$ ............................................... H01J 3/14
[52] U.S. Cl. ..................................... 250/216; 356/225
[58] Field of Search ............... 250/216, 226; 356/215, 356/225, 317, 442; 359/613, 614, 641

[56] References Cited

U.S. PATENT DOCUMENTS 3,619,623 11/1971 Huston ............................... 356/442
4,082,459 4/1978 Wolfe ................................. 356/317

Primary Examiner—David C. Nelms
Assistant Examiner—K. Shami
Attorney, Agent, or Firm—Finnegan, Henderson, Farabow, Garrett and Dunner

[57] ABSTRACT

In the photometer arrangement comprising a light source, lens system with beam splitter, measurement cell, scattered light trap and photodetector, said parts being arranged in this sequence, the scattered light trap comprises a honeycomb. The ratio between the free cross-section of its individual channels and the length thereof is from 1:40 to 1:300.

1 Claim, 1 Drawing Sheet

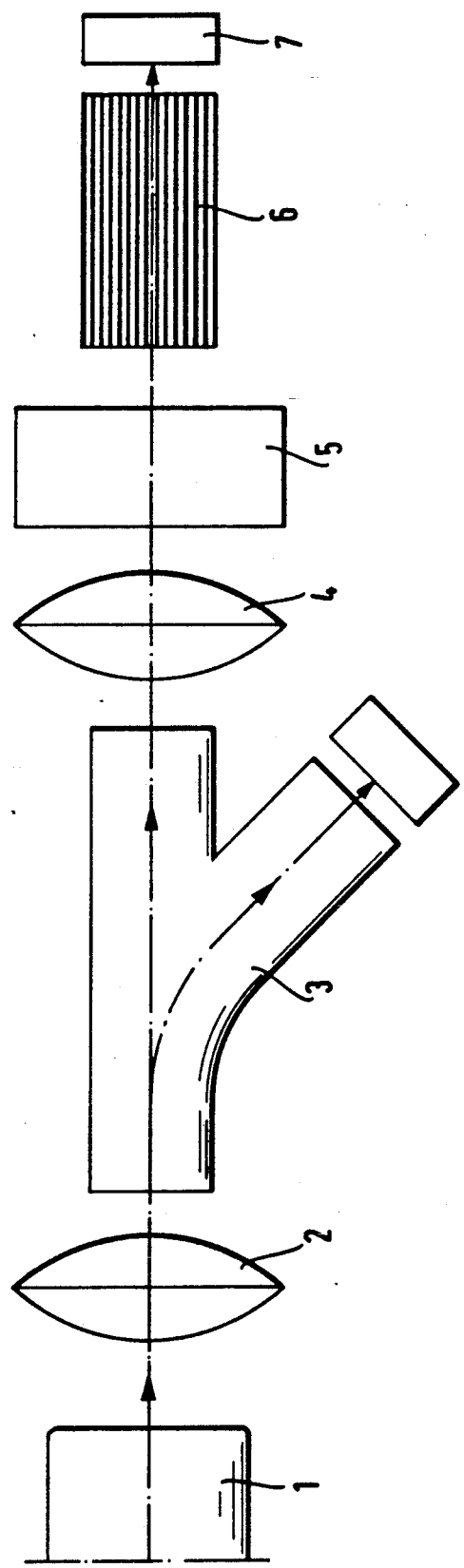

PHOTOMETER ARRANGEMENT WITH SCATTERED LIGHT TRAP

DESCRIPTION

The invention relates to a photometer arrangement comprising a light source, lens system with beam splitter, measurement cell, scattered light trap and photodetector, said parts being arranged in this sequence, for carrying out turbidity measurements.

Photometer arrangements in which a diaphragm system is arranged as a scattered light trap between the measurement cell and the photodetector are known in general terms. They have the disadvantage that, in order to limit the scattering angle, the length of the diaphragm system in the optical arrangement must be relatively long in order to measure light in the range of only a few degrees and to exclude scattered light at larger angles. The angle at which the remainder of the scattered light reaches the detector is in addition dependent on the point of origin in the cell.

When carrying out quantitative protein tests by the turbidometric method, in which the drop in intensity of the primary beam on passing through the measurement cell containing the protein is measured, scattered light arises simultaneously at the precipitates and latex agglutinates. The proportion of scattered light in the forward direction produces a signal contribution at the photodetector which counters the desired measurement signal from the concentration-dependent drop in intensity of the primary light and reduces the sensitivity of the measurement method.

The invention is intended to remedy this situation. The invention as claimed achieves the object in that the scattered light trap comprises a honeycomb in which the ratio between the free cross-section of its individual channels and the length thereof is from 1:40 to 1:300.

The invention allows the scattering angle in the forward direction to be limited to about ±1 degree, while the primary light passes through the scattered light trap virtually completely, ie. to the extent of its parallelity. Through the narrow, parallel channels of the honeycomb, oblique rays, such as the scattered light at the channel walls, are reflected and absorbed, if the walls are appropriately rough and/or colored. The maximum scattering angle at which a light ray hits the photodetector depends on the cross-section and length of an individual capillary of the honeycomb.

The invention is described in greater detail with reference to the drawing, which shows only one embodiment, with a diagrammatic representation of a photometer arrangement.

The light from a light source 1, for example a laser, passes through a lens system, comprising condenser 2, beam splitter 3 and lens 4, into the measurement cell 5, which contains the material to be measured. The primary beam exits the cell 5, possibly with reduced intensity, and, after passing through the light trap 6, hits the photodetector 7. Only an insignificant proportion of the forward-scattered light can pass through the light trap 6. Thus, for example if a honeycomb with a length of 56 mm and a wall thickness of 0.2 mm is used, only scattered light whose scattering angle deviates by less than ±1 degree from the optical axis escapes from its 1 mm broad channels to hit the photodetector 7; for a length of 22 mm, the scattering angle is less than ±4 degrees. The light trap, the honeycomb, can comprise ceramic, plastic or metal.

We claim:

1. A photometer arrangement comprising light source, lens system with beam splitter, measurement cell, scattered light trap and photodetector, said parts being arranged in this sequence, wherein the scattered light trap comprises a honeycomb in which the ratio between the free cross-section of its individual channels and the length thereof is from 1:40 to 1:300.

* * * * *